US009832305B2

(12) United States Patent
Du et al.

(10) Patent No.: US 9,832,305 B2
(45) Date of Patent: Nov. 28, 2017

(54) CONFIGURE SMARTPHONE BASED ON USER SLEEP STATUS

(71) Applicant: Intel Corporation, Santa Clara, CA (US)

(72) Inventors: Jianghong Du, Shanghai (CN); Yong Jiang, Shanghai (CN); Jim S Baca, Corrales, NM (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/779,512

(22) PCT Filed: Dec. 12, 2014

(86) PCT No.: PCT/CN2014/093694

§ 371 (c)(1),
(2) Date: Sep. 23, 2015

(87) PCT Pub. No.: WO2016/090630

PCT Pub. Date: Jun. 16, 2016

(65) Prior Publication Data

US 2016/0330311 A1 Nov. 10, 2016

(51) Int. Cl.

| | |
|---|---|
| ***H04M 1/00*** | (2006.01) |
| ***H04M 1/725*** | (2006.01) |
| ***G06F 1/16*** | (2006.01) |
| ***G06F 3/01*** | (2006.01) |

(Continued)

(52) U.S. Cl.

CPC ....... *H04M 1/72569* (2013.01); *A61B 5/0077* (2013.01); *A61B 5/01* (2013.01);

(Continued)

(58) Field of Classification Search

CPC ... A61B 5/0205; A61B 5/0022; A61B 5/0024; A61B 5/01; A61B 5/02405;

(Continued)

(56) References Cited

U.S. PATENT DOCUMENTS

2007/0068527 A1* 3/2007 Baker .................... A61B 5/00 128/204.23
2008/0167535 A1* 7/2008 Stivoric ............ G01R 29/0814 600/301

(Continued)

FOREIGN PATENT DOCUMENTS

CN 103637771 A 3/2014
CN 103870220 A 6/2014
CN 203858579 U 10/2014

OTHER PUBLICATIONS

"International Application Serial No. PCT/CN2014/093694, Written Opinion dated Sep. 18, 2015", 4 pgs.

(Continued)

*Primary Examiner* — Ajibola Akinyemi
(74) *Attorney, Agent, or Firm* — Schwegman Lundberg & Woessner, P.A.

(57) ABSTRACT

Various systems and methods for configuring a smartphone based on a user's sleep status are described herein. A compute device includes a determination module to determine a physiological state of a person and a configuration module to configure a quiet mode of the compute device based on the physiological state of the person.

24 Claims, 4 Drawing Sheets

(51) Int. Cl.
*A61B 5/00* (2006.01)
*A61B 5/01* (2006.01)
*A61B 5/024* (2006.01)
*G06F 3/16* (2006.01)
*H04M 3/42* (2006.01)
*H04M 1/02* (2006.01)

(52) U.S. Cl.
CPC ........ *A61B 5/02438* (2013.01); *A61B 5/4809* (2013.01); *A61B 5/6898* (2013.01); *G06F 1/1694* (2013.01); *G06F 3/015* (2013.01); *G06F 3/165* (2013.01); *H04M 3/42051* (2013.01); *A61B 2562/0219* (2013.01); *H04M 1/0264* (2013.01); *H04M 1/72527* (2013.01)

(58) Field of Classification Search
CPC .............. A61B 5/02438; A61B 5/0531; A61B 5/1118; A61B 5/165; A61B 5/4094; A61B 5/4806; A61B 5/08; A61B 5/20; A61B 5/40; A61B 5/41; A61B 5/42; A61B 5/43; A61B 5/44
USPC .......................................................... 455/567
See application file for complete search history.

(56) References Cited

U.S. PATENT DOCUMENTS

| | | | | |
|---|---|---|---|---|
| 2012/0254907 | A1* | 10/2012 | Serdiuk | A61B 5/0002 725/10 |
| 2014/0101296 | A1* | 4/2014 | Li | G06Q 30/02 709/221 |
| 2016/0089028 | A1* | 3/2016 | Chatterjee | A61B 5/0002 340/870.07 |

OTHER PUBLICATIONS

"International Application Serial No. PCT/CN2014/039694, Written Opinion dated Sep. 18, 2015", 4 pgs.

* cited by examiner

CONFIGURE SMARTPHONE BASED ON USER SLEEP STATUS

This patent application is a U.S. National Stage Application under 35 U.S.C. 371 from International Application PCT/CN2014/093694, filed Dec. 12, 2014, which is hereby incorporated by reference in its entirety.

TECHNICAL FIELD

Embodiments described herein generally relate to mobile phone management and in particular, to configuring a smartphone based on user sleep status.

BACKGROUND

Many mobile phones are configurable to operate in a normal mode or a quiet mode. In a normal mode the mobile phone may use an audible ring tone to notify the user of an incoming call, notifications, or the other alerts. In a quiet mode, such audible ring tones or alerts may be suppressed or reduced.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Mobile phones are eminently useful devices. They may be used by themselves or in conjunction with other devices. For example, a mobile phone may be paired with another device such as a Bluetooth headset or a vehicle infotainment system. When an incoming call is detected, the phone or an associated device may ring. Many phones provide a silent or quiet mode so that the user may reduce or eliminate the audible ringing. Such silent or quiet modes are typically enabled manually by the user. In some cases, the mobile phone may be configurable to enter and exit the silent/quiet mode on a schedule. For example, a user may configure a phone to enter silent mode at 11:00 PM and then resume the normal mode at 6:00 AM. While having a manual or scheduled mechanism to enter a silent mode is useful, it may be onerous for the user to constantly enter and exit silent mode manually or may provide unintended effects when the person's schedule is interrupted (e.g., by working late, attending a party, etc.). Exiting mechanisms fail to provide a flexible or intelligent solution.

The systems and methods described herein provide a mechanism to automatically shift between standard and silent modes in response to the user's real-time sleep status. In embodiments, the systems and methods monitor and sense a user's activity and when the user is determined to be asleep, the user's phone is transitioned to a silent or quiet mode. Using an adaptive mechanism addresses dynamic situations. For example, the user in the example previously discussed who has a scheduled silent mode from 11:00 PM to 6:00 AM may fall asleep early one night. In such an example, when the user is asleep at 10:00 PM, the user's phone may still use an audible ring. Although correctly following the provided configuration, the phone fails to provide the user experience that the user expects—that is, a quiet time when the user is asleep.

Figure 1:
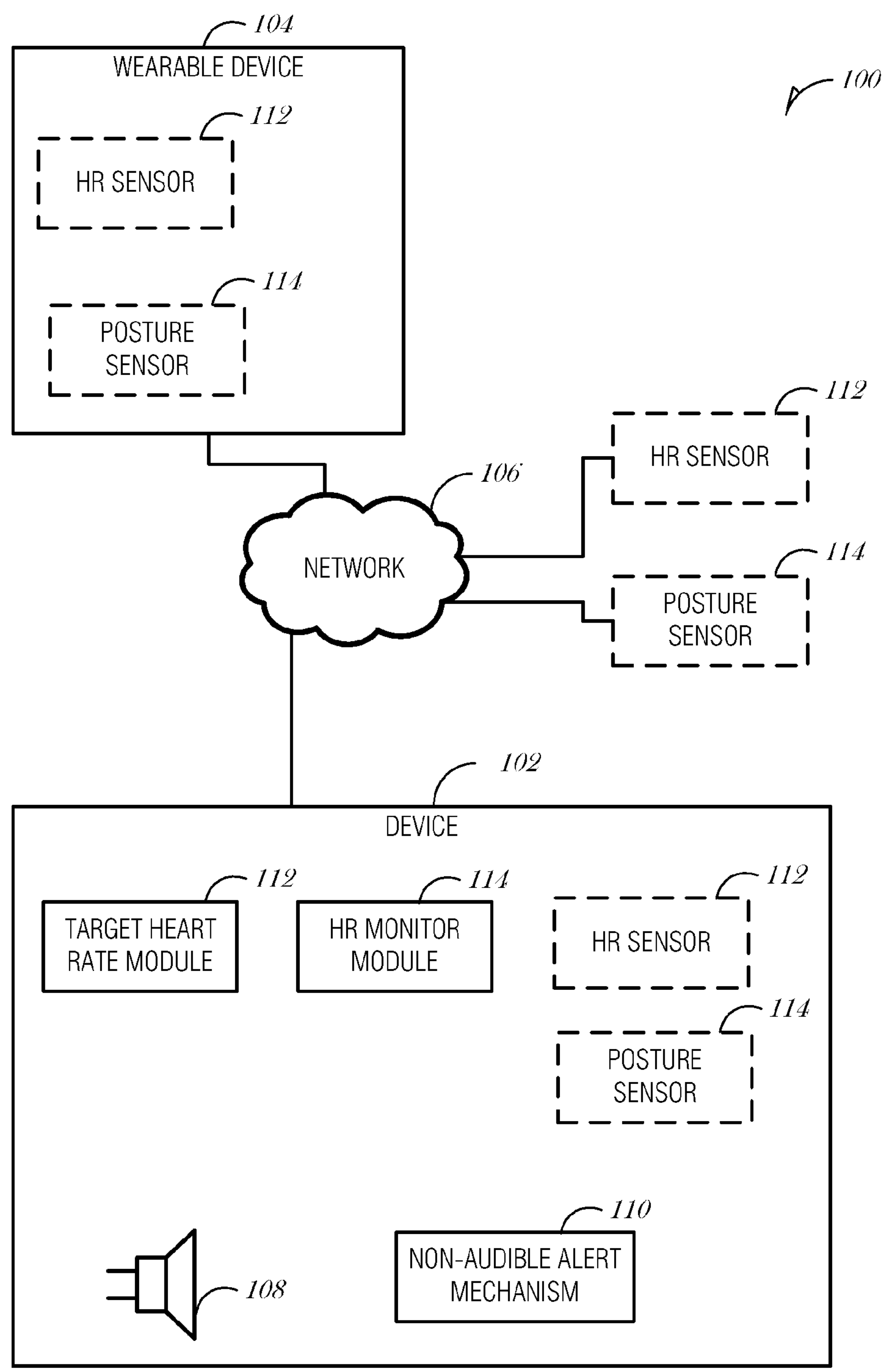
FIG. 1 is a schematic drawing illustrating a system, according to an embodiment.

FIG. 1 is a schematic drawing illustrating a system 100, according to an embodiment. The system 100 includes a compute device 102 and a wearable device 104, which are communicatively coupled via a network 106. The compute device 102 may be a device such as a smartphone, cellular telephone, mobile phone, laptop computer, tablet computer, music player, wearable device (e.g., watch, glasses-based device, etc.), desktop, laptop, hybrid, in-wall, or other networked device. The compute device 102 includes a speaker 108 and a non-audible alert mechanism 110. The non-audible alert mechanism 110 may be a mechanical vibration motor or an electronic display. When in a normal mode, the compute device 102 may alert a user of an incoming call or notification using the audible alert mechanism (e.g., a ringtone). When operating in silent mode, the compute device 102 may alert the user with a vibration or vibration pattern, a visual notification, or combinations of non-audible alerts.

The wearable device 104 may be remote from the compute device 102 or incorporated into the compute device 102. The wearable device 104 may be paired with the compute device 102 using a short-range wireless network, such as Bluetooth.

The network 106 may include local-area networks (LAN), wide-area networks (WAN), wireless networks (e.g., 802.11 or cellular network), the Public Switched Telephone Network (PSTN) network, ad hoc networks, personal area networks (e.g., Bluetooth) or other combinations or permutations of network protocols and network types. The network 106 may include a single local area network (LAN) or wide-area network (WAN), or combinations of LANs or WANs, such as the Internet. The various devices in FIG. 1 may be coupled to the network 106 via one or more wired or wireless connections.

The compute device 102 or the wearable device 104 may include a heart rate sensor 112. The heart rate sensor 112 may be incorporated into the compute device 102 or wearable device 104, or communicatively coupled to the compute device 102 or wearable device with a wired or wireless connection (e.g., via the network 106). The heart rate sensor 112 may be an optical sensor, such as a camera on the compute device 102 or an optical pulse monitoring sensor in a wearable device 104 (e.g., an earphone). The heart rate sensor 112 may also be a chest strap, wrist band, finger band, or other sensor to detect the user's heart rate.

A posture sensor 114, may be incorporated into the compute device 102 or wearable device 104, or operate independently. The posture sensor 114 may be used to determine whether a user is upright or lying down. Other sensors may also be used, such as infrared motion sensors, breathing sensors, acoustic sensors, or the like. As another example, a MEMS device may be used to sense whether the user is moving. Such activity monitoring may be performed using an accelerometer (e.g., a MEMS accelerometer), blood pressure sensor, heart rate sensor 112, skin temperature sensor, or the like. For example, if a user is stationary (e.g., as determined by an accelerometer), supine (e.g., as determined by a posture sensor 114), and relatively low heart rate (e.g., as determined by a heart rate sensor 112), the compute device 102 may be configured to a silent mode to reflect the possibility that the user is attempting to fall asleep or has fallen asleep. The time of day, location of the user, and other inputs may be used to confirm or invalidate this determination, and thus change the settings used.

Figure 2:
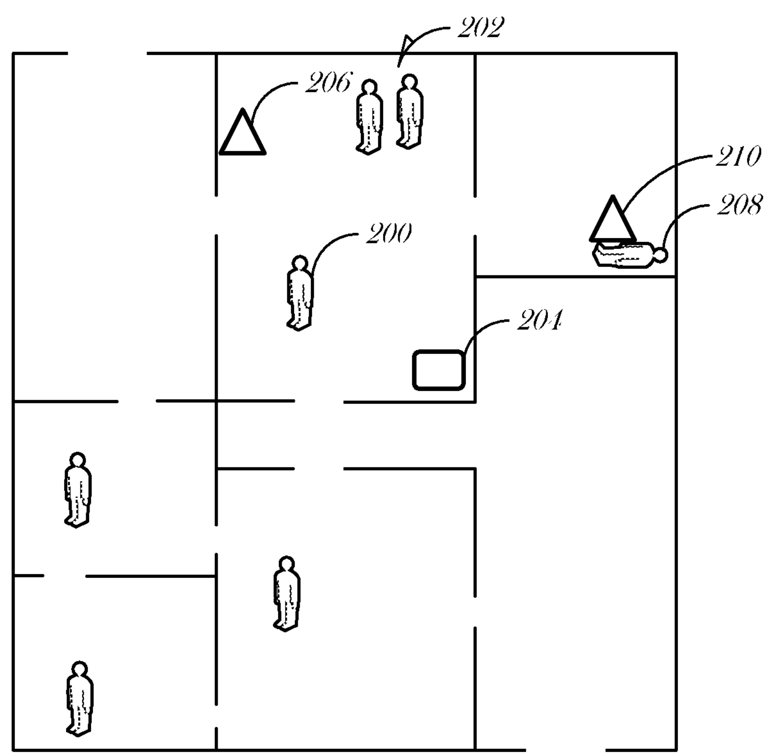
FIG. 2 is an example environment, according to various embodiments.

FIG. 2 is an example environment, according to various embodiments. One or more people 200 may be in a room 202. A device 204 may be located in the room 202. The device 204 may be any of a variety of devices, such as laptops, smartphones, entertainment systems, gaming systems, or the like. The device may be used to communicate, such with a phone call, Internet conference, or other forms of communication. The device 204 may notify a person 200 of an alert or notification, such as an incoming phone call, a text message being received, an appointment reminder, a timer expiring, or the like. The device 204 may be incorporated into a home automation system and alert a person 200 of various status messages (e.g., a security alarm). Further, although the example illustrated in FIG. 2 is a building, it is understood that the device 204 may be used in other contexts, such as in a vehicle.

One or more sensors 206 may also be used in or around the room 202. The sensor 206 may be incorporated into a device used by one of the people, such as a mobile device, a wearable device, or the like. The sensor 206 may also be incorporated into the room 202, such as with a wall-mounted camera, motion sensor, or the like.

The device 204 may be set to a silent or quiet mode from a regular mode using either push or pull mechanisms. As an illustration of a pull mechanism, a person 208 may be wearing a sensor 210 incorporated into a wrist-based wearable device. When the person 208 lies down to go to sleep, the sensor 210 in the wearable device may detect when the person 208 attains a restful state. The sensor 210 may detect slower breathing, reduced heart rate, a decrease in skin temperature, a prone or supine posture, reduced activity, lower blood pressure, changes in brain wave activity, or other indications that the person 208 has fallen asleep or is about to fall asleep. The sensor 210 may communicate the person's state to the device 204, resulting in a push notification from the sensor 210 to the device 204. In response, the device 204 reduces or eliminates audible notifications.

As an illustrating of a pull mechanism, the device 204 may periodically or recurrently poll one or more sensors 206 and 210 in or around the room 202 to detect when a person 200 and 208 is in a restful state (e.g., asleep or resting). When the device 204 receives information, the device 204 may use various inputs to determine when to transition to a quiet or silent mode.

The sensors 206 and 210 may be paired or otherwise communicatively coupled with the device 204. The device 204 may use a discovery protocol to identify sensors 206 and 210. A person 200 and 208 may configure the device 204 to react in a particular manner when placed into silent or quiet mode. For example, the person 200 and 208 may indicate certain applications on the device 204 that are put in silent mode, while leaving others in audible mode. Optionally, the device 204 may be placed entirely in a silent mode. As another example, the device's volume may be reduced instead of completely silenced. The volume reduction may be as a function of the distance the device 204 is from a resting person 208. For example, when the device 204 is near the resting person 208, the device 208 may be put in a silent mode. However, if the device 204 is in a different room or farther away from the resting person 208, the volume may be reduced but not muted. The farther away the device 204 is from the resting person 208, the less volume reduction may be used.

Several example usages are illustrated here involving a hypothetical user, Mary. As one example, Mary may be used to reading a book before sleeping. Sometimes she goes to sleep inadvertently, such as while reading. Her smart bracelet may detect that she is in sleep, communicate with her smartphone on her bedside table, which goes to sleep mode. The smartphone may turn off the cellular (e.g., 3G) and wireless local area network (e.g., Wi-Fi) radios to save power in addition to muting alerts. In the morning when Mary wakes up, the smart bracelet detects it and sends a message to her smartphone, which transitions to a standard notification mode and enables the radios.

As another example, Mary's little baby is going to sleep and Mary sits nearby and surfs the Internet on a tablet computer. Wearing a smart bracelet, the baby is detected as being asleep and sends message to Mary's tablet computer. Mary's tablet computer automatically goes to vibrate mode such that when receiving an alert (e.g., a new text message or a reminder for an appointment), Mary is notified without disturbing the baby.

As another example, Mary may set a configuration in her phone so that once she falls off to deep sleep, the phone turns off the 3G and Wi-Fi radios; if in light sleep, the phone is configured to just turn off Wi-Fi and keep the 3G radio on. Mary may also define which applications (e.g. chat, email application which will pull message) should turn off during light sleep or deep sleep.

As another example, Mary is a doctor and she needs be reachable by phone at any time during the day. Mary may set a policy on her smartphone to audibly ring when a call is incoming from the hospital that she works, but for calls from other people, the phone will only vibrate.

Figure 3:
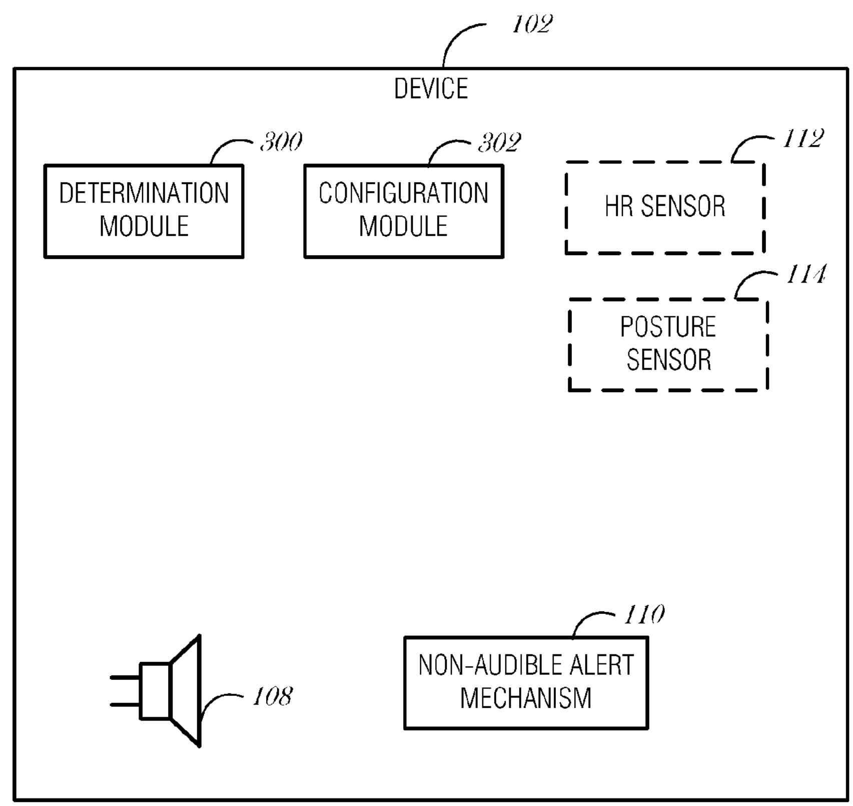
FIG. 3 is a block diagram illustrating a compute device, according to an embodiment.

FIG. 3 is a block diagram illustrating a compute device 102, according to an embodiment. The compute device 102 may include a determination module 300 and a configuration module 302. The determination module 300 may be configured to determine a physiological state of a person.

In an embodiment, to determine the physiological state of the person, the determination module 300 is to access a sensor to obtain sensor data and use the sensor data to determine the physiological state. In an embodiment, to access the sensor, the determination module 300 is to poll the sensor and obtain the sensor data in response to the polling. This is a pull mechanism (from the perspective of the sensor). In another embodiment, to obtain the sensor data, the determination module 300 is to listen for sensor data and receive the sensor data from the sensor. This is a push mechanism (from the perspective of the sensor).

In another embodiment, the determination module 300 uses contextual information to strengthen an inference of the physiological state of the person. For example, the determination module 300 may access the current time determine that it coincides with the person's regular bedtime or sleeping time. Other contextual information may be used, such as the person's calendar, appointments, social media posts, etc.

In an embodiment, the sensor is separate from the compute device 102. In another embodiment, the sensor is incorporated into the compute device 102. In embodiments, the sensor is one of a camera, a heart rate sensor, a skin temperature sensor, or an accelerometer.

In an embodiment, the sensor includes a heart rate sensor, and the sensor data includes a heart rate of the person, and to use the sensor data to determine the physiological state, the determination module 300 is to determine whether the heart rate is slower than a threshold rate and when the heart rate is slower than the threshold rate, declare that the physiological state of the person is resting.

In an embodiment, the sensor includes a posture sensor, and the sensor data includes an indication that the person is prone or supine, and to use the sensor data to determine the physiological state, the determination module 300 is to determine a duration the person has been prone or supine for longer than a threshold period and when the duration is longer than the threshold period, declare that the physiological state of the person is resting.

The configuration module 302 may be configured to configure a quiet mode of the compute device 102 based on the physiological state of the person.

In an embodiment, to configure the quiet mode of the compute device 102, the configuration module 302 is to mute a selection of applications executing on the compute device 102. In another embodiment, to configure the quiet mode of the compute device 102, the configuration module 302 is to determine a distance from the person to the compute device 102 and configure an audio volume of the compute device 102 as a function of the distance.

In an embodiment, to configure the quiet mode of the compute device 102, the configuration module 302 is to configure an application executing on the compute device 102 to selectively use an audible notification when the compute device 102 is in the quiet mode. For example, email notifications may be muted, but phone calls may continue to use an audible ring. In an embodiment, the application executing on the compute device 102 is a telephone application, and to selectively use the audible notification, the configuration module 302 is to selectively use an audible ringtone for an incoming call when the incoming call is from a certain caller.

Various modules (e.g., modules 300 and 302) may be incorporated or integrated into an application that executes on the compute device 102. The application may execute in the background and collect data from the sensors and populate a database, which may be accessed by one or more other applications. Multiple applications may be developed to use the real-time or historical data for various purposes.

Figure 4:
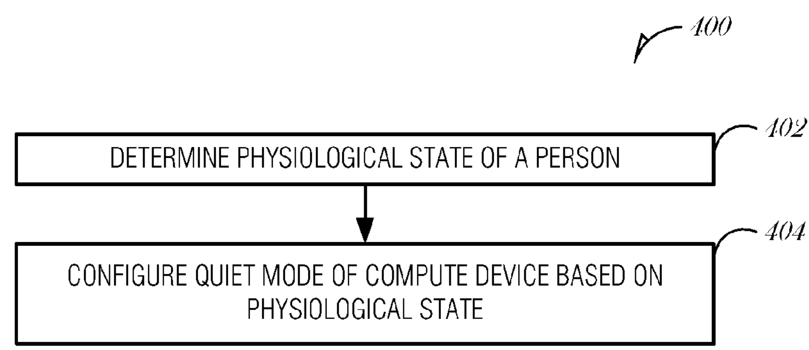
FIG. 4 is a flowchart illustrating a method for configuring a notification mode, according to an embodiment.

FIG. 4 is a flowchart illustrating a method 400 for configuring a notification mode, according to an embodiment. At 402, a physiological state of a person is determined at a compute device. In an embodiment, determining the physiological state of the person comprises accessing a sensor to obtain sensor data and using the sensor data to determine the physiological state. In an embodiment, accessing the sensor comprises polling the sensor and obtaining the sensor data in response to the polling. In another embodiment, obtaining the sensor data comprises listening for sensor data and receiving the sensor data from the sensor.

In an embodiment, determining the physiological state of the person comprises using contextual information to strengthen an inference of the physiological state of the person.

In an embodiment, the sensor is separate from the compute device. In another embodiment, the sensor is incorporated into the compute device. In embodiments, the sensor is one of a camera, a heart rate sensor, a skin temperature sensor, or an accelerometer.

In an embodiment, the sensor includes a heart rate sensor, and the sensor data includes a heart rate of the person. In such an embodiment, using the sensor data to determine the physiological state comprises determining whether the heart rate is slower than a threshold rate and when the heart rate is slower than the threshold rate, declaring that the physiological state of the person is resting.

In an embodiment, the sensor includes a posture sensor and the sensor data includes an indication that the person is prone or supine. In such an embodiment, using the sensor data to determine the physiological state comprises determining a duration that the person has been prone or supine for longer than a threshold period and when the duration is longer than the threshold period, declaring that the physiological state of the person is resting.

At block 404, a quiet mode of the compute device is configured based on the physiological state of the person. In an embodiment, configuring the quiet mode of the compute device comprises muting a selection of applications executing on the compute device. The selection of applications may be configured by a user of the compute device.

In an embodiment, configuring the quiet mode of the compute device comprises determining a distance from the person to the compute device and configuring an audio volume of the compute device as a function of the distance.

In an embodiment, configuring the quiet mode of the compute device comprises configuring an application executing on the compute device to selectively use an audible notification when the compute device is in the quiet mode. In an embodiment, the application executing on the compute device is a telephone application, and selectively using the audible notification comprises selectively using an audible ringtone for an incoming call when the incoming call is from a certain caller.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

Examples, as described herein, may include, or may operate on, logic or a number of components, modules, or mechanisms. Modules may be hardware, software, or firmware communicatively coupled to one or more processors in order to carry out the operations described herein. Modules may hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 5:
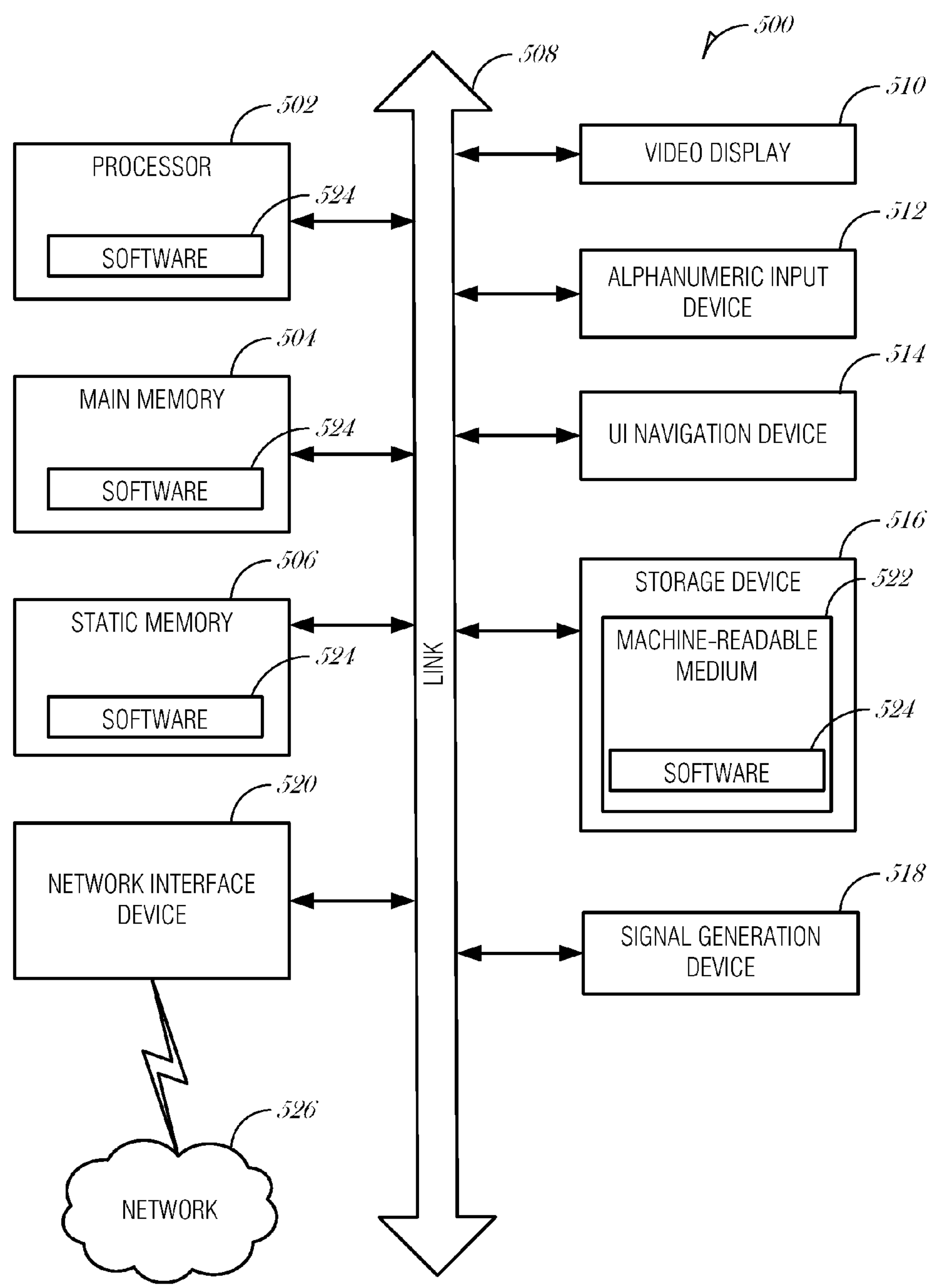
FIG. 5 is a block diagram illustrating an example machine upon which any one or more of the techniques (e.g., methodologies) discussed herein may perform, according to an example embodiment.

FIG. 5 is a block diagram illustrating a machine in the example form of a computer system 500, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be an onboard vehicle system, wearable device, personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 500 includes at least one processor 502 (e.g., a central processing unit (CPU), a graphics processing unit (GPU) or both, processor cores, compute nodes, etc.), a main memory 504 and a static memory 506, which communicate with each other via a link 508 (e.g., bus). The computer system 500 may further include a video display unit 510, an alphanumeric input device 512 (e.g., a keyboard), and a user interface (UI) navigation device 514 (e.g., a mouse). In one embodiment, the video display unit 510, input device 512 and UI navigation device 514 are incorporated into a touch screen display. The computer system 500 may additionally include a storage device 516 (e.g., a drive unit), a signal generation device 518 (e.g., a speaker), a network interface device 520, and one or more sensors (not shown), such as a global positioning system (GPS) sensor, compass, accelerometer, or other sensor.

The storage device 516 includes a machine-readable medium 522 on which is stored one or more sets of data structures and instructions 524 (e.g., software) embodying or utilized by any one or more of the methodologies or functions described herein. The instructions 524 may also reside, completely or at least partially, within the main memory 504, static memory 506, and/or within the processor 502 during execution thereof by the computer system 500, with the main memory 504, static memory 506, and the processor 502 also constituting machine-readable media.

While the machine-readable medium 522 is illustrated in an example embodiment to be a single medium, the term "machine-readable medium" may include a single medium or multiple media (e.g., a centralized or distributed database, and/or associated caches and servers) that store the one or more instructions 524. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Additional Notes & Examples

Example 1 includes subject matter (such as a device, apparatus, or machine) comprising a compute device comprising: a determination module to determine a physiological state of a person; and a configuration module to configure a quiet mode of the compute device based on the physiological state of the person.

In Example 2, the subject matter of Example 1 may include, wherein to determine the physiological state of the person, the determination module is to: use contextual information to strengthen an inference of the physiological state of the person.

In Example 3, the subject matter of any one of Examples 1 to 2 may include, wherein to determine the physiological state of the person, the determination module is to: access a sensor to obtain sensor data; and use the sensor data to determine the physiological state.

In Example 4, the subject matter of any one of Examples 1 to 3 may include, wherein the sensor is separate from the compute device.

In Example 5, the subject matter of any one of Examples 1 to 4 may include, wherein the sensor is incorporated into the compute device.

In Example 6, the subject matter of any one of Examples 1 to 5 may include, wherein the sensor is one of a camera, a heart rate sensor, a skin temperature sensor, or an accelerometer.

In Example 7, the subject matter of any one of Examples 1 to 6 may include, wherein the sensor includes a heart rate sensor, and wherein the sensor data includes a heart rate of the person, and wherein to use the sensor data to determine the physiological state, the determination module is to: determine whether the heart rate is slower than a threshold rate; and when the heart rate is slower than the threshold rate, declare that the physiological state of the person is resting.

In Example 8, the subject matter of any one of Examples 1 to 7 may include, wherein the sensor includes a posture sensor, and wherein the sensor data includes an indication that the person is prone or supine, and to use the sensor data to determine the physiological state, the determination module is to: determine a duration the person has been prone or supine for longer than a threshold period; and when the duration is longer than the threshold period, declare that the physiological state of the person is resting.

In Example 9, the subject matter of any one of Examples 1 to 8 may include, wherein to access the sensor, the determination module is to: poll the sensor; and obtain the sensor data in response to the polling.

In Example 10, the subject matter of any one of Examples 1 to 9 may include, wherein to obtain the sensor data, the determination module is to: listen for sensor data; and receive the sensor data from the sensor.

In Example 11, the subject matter of any one of Examples 1 to 10 may include, wherein to configure the quiet mode of the compute device, the configuration module is to mute a selection of applications executing on the compute device.

In Example 12, the subject matter of any one of Examples 1 to 11 may include, wherein to configure the quiet mode of the compute device, the configuration module is to: determine a distance from the person to the compute device; and configure an audio volume of the compute device as a function of the distance.

In Example 13, the subject matter of any one of Examples 1 to 12 may include, wherein to configure the quiet mode of the compute device, the configuration module is to configure an application executing on the compute device to selectively use an audible notification when the compute device is in the quiet mode.

In Example 14, the subject matter of any one of Examples 1 to 13 may include, wherein the application executing on the compute device is a telephone application, and wherein to selectively use the audible notification, the configuration module is to selectively use an audible ringtone for an incoming call when the incoming call is from a certain caller.

Example 15 includes subject matter for configuring a notification mode (such as a method, means for performing acts, machine readable medium including instructions that when performed by a machine cause the machine to performs acts, or an apparatus to perform) comprising: determining, at a compute device, a physiological state of a person; and configuring a quiet mode of the compute device based on the physiological state of the person.

In Example 16, the subject matter of Example 15 may include, wherein determining the physiological state of the person comprises: using contextual information to strengthen an inference of the physiological state of the person.

In Example 17, the subject matter of any one of Examples 15 to 16 may include, wherein determining the physiological state of the person comprises: accessing a sensor to obtain sensor data; and using the sensor data to determine the physiological state.

In Example 18, the subject matter of any one of Examples 15 to 17 may include, wherein the sensor is separate from the compute device.

In Example 19, the subject matter of any one of Examples 15 to 18 may include, wherein the sensor is incorporated into the compute device.

In Example 20, the subject matter of any one of Examples 15 to 19 may include, wherein the sensor is one of a camera, a heart rate sensor, a skin temperature sensor, or an accelerometer.

In Example 21, the subject matter of any one of Examples 15 to 20 may include, wherein the sensor includes a heart rate sensor, and wherein the sensor data includes a heart rate of the person, and wherein using the sensor data to determine the physiological state comprises: determining whether the heart rate is slower than a threshold rate; and when the heart rate is slower than the threshold rate, declaring that the physiological state of the person is resting.

In Example 22, the subject matter of any one of Examples 15 to 21 may include, wherein the sensor includes a posture sensor, and wherein the sensor data includes an indication that the person is prone or supine, and wherein using the sensor data to determine the physiological state comprises: determining a duration the person has been prone or supine for longer than a threshold period; and when the duration is longer than the threshold period, declaring that the physiological state of the person is resting.

In Example 23, the subject matter of any one of Examples 15 to 22 may include, wherein accessing the sensor comprises: polling the sensor; and obtaining the sensor data in response to the polling.

In Example 24, the subject matter of any one of Examples 15 to 23 may include, wherein obtaining the sensor data comprises: listening for sensor data; and receiving the sensor data from the sensor.

In Example 25, the subject matter of any one of Examples 15 to 24 may include, wherein configuring the quiet mode of the compute device comprises muting a selection of applications executing on the compute device.

In Example 26, the subject matter of any one of Examples 15 to 25 may include, wherein configuring the quiet mode of the compute device comprises: determining a distance from the person to the compute device; and configuring an audio volume of the compute device as a function of the distance.

In Example 27, the subject matter of any one of Examples 15 to 26 may include, wherein configuring the quiet mode of the compute device comprises configuring an application executing on the compute device to selectively use an audible notification when the compute device is in the quiet mode.

In Example 28, the subject matter of any one of Examples 15 to 27 may include, wherein the application executing on the compute device is a telephone application, and wherein selectively using the audible notification comprises selectively using an audible ringtone for an incoming call when the incoming call is from a certain caller.

Example 29 includes at least one machine-readable medium including instructions, which when executed by a machine, cause the machine to perform operations of any of the Examples 15-28.

Example 30 includes an apparatus comprising means for performing any of the Examples 15-28.

Example 31 includes subject matter for configuring a notification mode (such as a device, apparatus, or machine) comprising: means for determining, at a compute device, a physiological state of a person; and means for configuring a quiet mode of the compute device based on the physiological state of the person.

In Example 32, the subject matter of Example 31 may include, wherein the means for determining the physiological state of the person comprise: means for using contextual information to strengthen an inference of the physiological state of the person.

In Example 33, the subject matter of any one of Examples 31 to 32 may include, wherein the means for determining the physiological state of the person comprise: means for accessing a sensor to obtain sensor data; and means for using the sensor data to determine the physiological state.

In Example 34, the subject matter of any one of Examples 31 to 33 may include, wherein the sensor is separate from the compute device.

In Example 35, the subject matter of any one of Examples 31 to 34 may include, wherein the sensor is incorporated into the compute device.

In Example 36, the subject matter of any one of Examples 31 to 35 may include, wherein the sensor is one of a camera, a heart rate sensor, a skin temperature sensor, or an accelerometer.

In Example 37, the subject matter of any one of Examples 31 to 36 may include, wherein the sensor includes a heart rate sensor, and wherein the sensor data includes a heart rate of the person, and wherein the means for using the sensor data to determine the physiological state comprise: means for determining whether the heart rate is slower than a threshold rate; and means for declaring that the physiological state of the person is resting when the heart rate is slower than the threshold rate.

In Example 38, the subject matter of any one of Examples 31 to 37 may include, wherein the sensor includes a posture sensor, and wherein the sensor data includes an indication that the person is prone or supine, and wherein the means for using the sensor data to determine the physiological state comprise: means for determining a duration the person has been prone or supine for longer than a threshold period; and means for declaring that the physiological state of the person is resting when the duration is longer than the threshold period.

In Example 39, the subject matter of any one of Examples 31 to 38 may include, wherein the means for accessing the sensor comprise: means for polling the sensor; and means for obtaining the sensor data in response to the polling.

In Example 40, the subject matter of any one of Examples 31 to 39 may include, wherein the means for obtaining the sensor data comprise: means for listening for sensor data; and means for receiving the sensor data from the sensor.

In Example 41, the subject matter of any one of Examples 31 to 40 may include, wherein the means for configuring the quiet mode of the compute device comprise means for muting a selection of applications executing on the compute device.

In Example 42, the subject matter of any one of Examples 31 to 41 may include, wherein the means for configuring the quiet mode of the compute device comprise: means for determining a distance from the person to the compute device; and means for configuring an audio volume of the compute device as a function of the distance.

In Example 43, the subject matter of any one of Examples 31 to 42 may include, wherein the means for configuring the quiet mode of the compute device comprise means for configuring an application executing on the compute device to selectively use an audible notification when the compute device is in the quiet mode.

In Example 44, the subject matter of any one of Examples 31 to 43 may include, wherein the application executing on the compute device is a telephone application, and wherein the means for selectively using the audible notification comprise means for selectively using an audible ringtone for an incoming call when the incoming call is from a certain caller.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure, for example, to comply with 37 C.F.R. §1.72(b) in the United States of America. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A compute device comprising:
a determination module to determine a physiological state of a person; and
a configuration module to configure a quiet mode of the compute device based on the physiological state of the person, wherein to configure the quiet mode of the compute device, the configuration module is to:
determine a distance from the person to the compute device;
configure an audio volume of the compute device as a function of the distance; and
configure an application executing on the compute device to selectively use an audible notification when the compute device is in the quiet mode.

2. The compute device of claim 1, wherein to determine the physiological state of the person, the determination module is to:
use contextual information to strengthen an inference of the physiological state of the person.

3. The compute device of claim 1, wherein to determine the physiological state of the person, the determination module is to:
access a sensor to obtain sensor data; and
use the sensor data to determine the physiological state.

4. The compute device of claim 3, wherein the sensor is separate from the compute device.

5. The compute device of claim 3, wherein the sensor is incorporated into the compute device.

6. The compute device of claim 5, wherein the sensor is one of a camera, a heart rate sensor, a skin temperature sensor, or an accelerometer.

7. The compute device of claim 3, wherein the sensor includes a heart rate sensor, and wherein the sensor data includes a heart rate of the person, and wherein to use the sensor data to determine the physiological state, the determination module is to:
determine whether the heart rate is slower than a threshold rate; and
when the heart rate is slower than the threshold rate, declare that the physiological state of the person is resting.

8. The compute device of claim 3, wherein the sensor includes a posture sensor, and wherein the sensor data includes an indication that the person is prone or supine, and to use the sensor data to determine the physiological state, the determination module is to:
determine a duration the person has been prone or supine for longer than a threshold period; and
when the duration is longer than the threshold period, declare that the physiological state of the person is resting.

9. The compute device of claim 3, wherein to access the sensor, the determination module is to:
poll the sensor; and
obtain the sensor data in response to the polling.

10. The compute device of claim 3, wherein to obtain the sensor data, the determination module is to:
listen for sensor data; and
receive the sensor data from the sensor.

11. The compute device of claim 1, wherein to configure the quiet mode of the compute device, the configuration module is to mute a selection of applications executing on the compute device.

12. The compute device of claim 1, wherein the application executing on the compute device is a telephone application, and wherein to selectively use the audible notification, the configuration module is to selectively use an audible ringtone for an incoming call when the incoming call is from a certain caller.

13. The compute device of claim 1, wherein to configure the audio volume of the compute device as the function of the distance, the configuration module is to use a louder volume as the distance increases.

14. A method of configuring a notification mode, the method comprising:
determining, at a compute device, a physiological state of a person; and
configuring a quiet mode of the compute device based on the physiological state of the person, wherein configuring the quiet mode of the compute device comprises:
determining a distance from the person to the compute device;
configuring an audio volume of the compute device as a function of the distance; and
configuring an application executing on the compute device to selectively use an audible notification when the compute device is in the quiet mode.

15. The method of claim 14, wherein determining the physiological state of the person comprises:
using contextual information to strengthen an inference of the physiological state of the person.

16. The method of claim 14, wherein determining the physiological state of the person comprises:
accessing a sensor to obtain sensor data; and
using the sensor data to determine the physiological state.

17. The method of claim 14, wherein the application executing on the compute device is a telephone application, and wherein selectively using the audible notification comprises selectively using an audible ringtone for an incoming call when the incoming call is from a certain caller.

18. At least one non-transitory machine-readable medium including instructions for configuring a notification mode, which when executed by a machine, cause the machine to:
determine, at a compute device, a physiological state of a person; and
configure a quiet mode of the compute device based on the physiological state of the person, wherein the instructions to configure the quiet mode of the compute device comprise instructions to:
determine a distance from the person to the compute device;
configure an audio volume of the compute device as a function of the distance; and
configure an application executing on the compute device to selectively use an audible notification when the compute device is in the quiet mode.

19. The at least one machine-readable medium of claim 18, wherein the instructions to determine the physiological state of the person comprise instructions to:
use contextual information to strengthen an inference of the physiological state of the person.

20. The at least one machine-readable medium of claim 18, wherein the instructions to determine the physiological state of the person comprise instructions to:
access a sensor to obtain sensor data; and
use the sensor data to determine the physiological state.

21. The at least one machine-readable medium of claim 20, wherein the sensor includes a heart rate sensor, and wherein the sensor data includes a heart rate of the person, and wherein the instructions to using the sensor data to determine the physiological state comprise instructions to:

determine whether the heart rate is slower than a threshold rate; and when the heart rate is slower than the threshold rate, declare that the physiological state of the person is resting.

22. The at least one machine-readable medium of claim 20, wherein the sensor includes a posture sensor, and wherein the sensor data includes an indication that the person is prone or supine, and wherein the instructions to using the sensor data to determine the physiological state comprise instructions to:

determine a duration the person has been prone or supine for longer than a threshold period; and when the duration is longer than the threshold period, declare that the physiological state of the person is resting.

23. The at least one machine-readable medium of claim 18, wherein the application executing on the compute device is a telephone application, and wherein the instructions to selectively use the audible notification comprise instructions to selectively use an audible ringtone for an incoming call when the incoming call is from a certain caller.

24. The at least one machine-readable medium of claim 18, wherein the instructions to configure the audio volume of the compute device as the function of the distance comprise instructions to use a louder volume as the distance increases.

* * * * *

UNITED STATES PATENT AND TRADEMARK OFFICE

CERTIFICATE OF CORRECTION

PATENT NO. : 9,832,305 B2
APPLICATION NO. : 14/779512
DATED : November 28, 2017
INVENTOR(S) : Du et al.

It is certified that error appears in the above-identified patent and that said Letters Patent is hereby corrected as shown below:

On the Title Page

On page 2, in Column 2, item (56), under "Other Publications", Lines 1-2, delete "Written Opinion" and insert --International Search Report-- therefor Signed and Sealed this
Eleventh Day of June, 2019

Andrei Iancu
*Director of the United States Patent and Trademark Office*